(12) United States Patent
Zuhars et al.

(10) Patent No.: US 7,997,474 B2
(45) Date of Patent: Aug. 16, 2011

(54) SYSTEM AND METHOD FOR CONFIGURING A MEDICAL DEVICE

(75) Inventors: Joel Zuhars, Haverhill, MA (US); Daniel Groszmann, Cambridge, MA (US)

(73) Assignee: General Electric Company, Schenectady, NY (US)

( * ) Notice: Subject to any disclaimer, the term of this patent is extended or adjusted under 35 U.S.C. 154(b) by 890 days.

(21) Appl. No.: 11/766,416

(22) Filed: Jun. 21, 2007

(65) Prior Publication Data

US 2008/0314973 A1   Dec. 25, 2008

(51) Int. Cl.
*G06F 17/00* (2006.01)
(52) U.S. Cl. ....................................... 235/375
(58) Field of Classification Search ............ 235/375
See application file for complete search history.

(56) References Cited

U.S. PATENT DOCUMENTS

| | | | |
|---|---|---|---|
| 5,368,562 A * | 11/1994 | Blomquist et al. | 604/65 |
| 7,317,955 B2 * | 1/2008 | McGreevy | 700/83 |
| 2002/0038392 A1 * | 3/2002 | De La Huerga | 710/8 |
| 2002/0169636 A1 * | 11/2002 | Eggers et al. | 705/3 |
| 2003/0140928 A1 * | 7/2003 | Bui et al. | 128/898 |
| 2004/0243434 A1 | 12/2004 | Peterka et al. | |
| 2005/0180615 A1 | 8/2005 | Gerder | |

FOREIGN PATENT DOCUMENTS

| | | |
|---|---|---|
| FR | 2866459 A1 | 8/2005 |
| WO | 2005031631 A2 | 4/2005 |

OTHER PUBLICATIONS

Search Report and Written Opinion from corresponding application FR0854102, Jan. 10, 2011.

* cited by examiner

*Primary Examiner* — Jamara A Franklin
(74) *Attorney, Agent, or Firm* — Kirton & McConkie; Kenneth E. Horton

(57) ABSTRACT

In one embodiment a medical device comprising an interface, a portable component and a controller is provided. The interface is configured for receiving identification data of a user, the portable component is configured for storing configuration data and the controller is configured for retrieving the configuration data based on the identification data and for configuring the medical device based on the configuration data.

25 Claims, 2 Drawing Sheets

SYSTEM AND METHOD FOR CONFIGURING A MEDICAL DEVICE

FIELD OF INVENTION

The invention relates, in general, to systems and methods for configuring a medical device and, in particular, to systems and methods using portable components to store data for configuring a medical device.

BACKGROUND OF THE INVENTION

A medical device is typically configured in preparation for a medical procedure. Medical devices require certain inputs before the medical procedure can be performed. For example, patient data (e.g., name, age, sex, etc.), medical procedure data (e.g. type of the medical procedure, body part, etc.), medical device settings (e.g., power, duration, etc.), confirmation of a user's (such as a medical staff's) preferred settings, service personnel inputs (e.g., calibration and maintenance records, software updates) and other such inputs.

Medical device inputs are typically performed via a user interface such as a keyboard and a mouse and/or file transports through a USB port, Ethernet, a printer, CD, floppy disk, etc. In other words, inputs are manually captured via the interface and originate as recorded entries by the user. The manually captured inputs have the disadvantage of requiring additional manual steps prior to or during the medical procedure, thus requiring additional time and resources to perform. This may result in a possibility for error in inputting the information into the medical device, as well as a concurrent delay in performing the medical procedure caused by manual entry of the data. The flow of the medical procedure is thus disrupted and the efficiency and time-management of the user (such as a surgeon) is reduced.

The user such as a surgeon and/or a medical staff often have specific preferences regarding the operation of a medical device during a given medical procedure particularly when the medical device is providing information related to or part of a medical workflow. User-specific configuration data being configuration data specific to the user can be used to customize the user experience when such data is available. An example of the user specific configuration data includes a particular sequence of GUI screen layouts that each contain a specific subset of information from an otherwise broader set of available information, such as particular sets of instrument tracking display types, that are of particular interest at different medical workflow steps. Another example of the user specific configuration data includes configurably applied rules or parameters for switching the medical workflow steps. The user specific configuration data facilitates customization of the medical device and thereby improves visibility of each particular information subset, reduces screen clutter, and reduces the required system interaction by the user, which is of particular value in the sterile and time-critical medical procedure setting.

Further, there may be multiple users for a single medical device, and therefore differentiation of the users is desired in order to select an appropriate configuration data for each user. Moreover, differentiation of user type is also of interest, as there may be general workflow differences that can be realized for different sets of users. For example, a medical workflow for a service user may be different from a general workflow for a clinical user. In addition, in order to add customizations for new users, and/or to modify data and/or add new data for existing users, the user specific configuration data is to be manually transported into the medical device.

Therefore, a need exists for a system and method for configuring a medical device that can provide the user specific configuration data to the medical device to reduce the user's interaction with the medical device thereby facilitating the user to carry out the medical procedure.

BRIEF DESCRIPTION OF THE INVENTION

The above-mentioned shortcomings, disadvantages and problems are addressed herein which will be understood by reading and understanding the following specification.

In one embodiment, a medical device is provided. The medical device comprises an interface for receiving identification data, a portable component for storing configuration data and a controller for retrieving the configuration data based on the identification data. The controller is further operable for configuring the medical device based on the configuration data.

In another embodiment, a method for configuring a medical device is provided. The method comprises providing a portable component operable to store configuration data, receiving an identification data at an interface, determining at a controller in the medical device whether a user associated with the identification data is authorized to use the medical device based on the identification data received at the interface, retrieving the configuration data from the portable component based on the identification data and configuring the medical device based on the configuration data retrieved.

In yet another embodiment, a computer program product stored in a computer readable media for providing a method for configuring a medical device is provided. The computer program product comprises a routine for receiving configuration data stored in a portable component, a routine for receiving an identification data at an interface operable to receive the identification data in the medical device, a routine for determining at a controller in the medical device whether a user associated with the identification data is authorized to use the medical device based on the identification data received at the interface, a routine for retrieving the configuration data from the portable component based on the identification data and a routine for configuring the medical device based on the configuration data retrieved.

Systems and methods of varying scope are described herein. In addition to the aspects and advantages described in the summary, further aspects and advantages will become apparent by reference to the drawings and with reference to the detailed description that follows.

DETAILED DESCRIPTION OF THE INVENTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
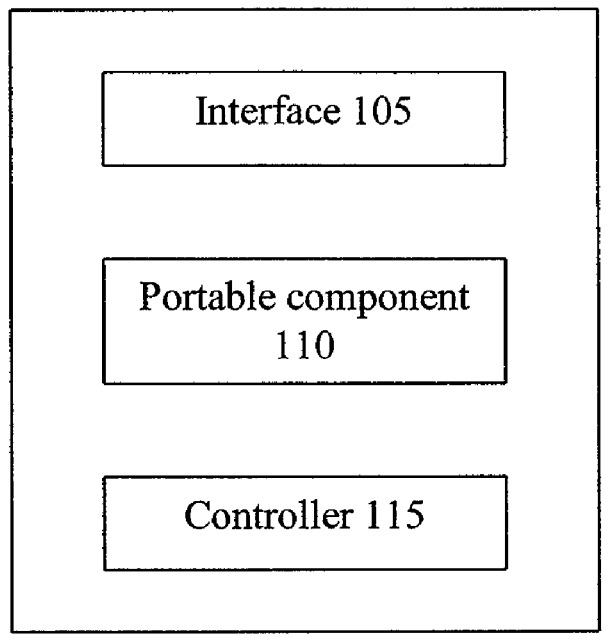
FIG. 1 shows a block diagram of a medical device, in an embodiment.

In one embodiment, as shown in FIG. 1, a medical device 100 comprising an interface 105, a portable component 110 and a controller 115 is provided. The medical device 100 can be a surgical device such as an ophthalmic laser device, a vitro retinal surgical device, a refractive laser eye surgery system and a phacoemulsification system. A person of skill in the art will realize that other medical devices can also be used.

The interface 105 of the medical device 100 is configured for receiving identification data of a user. The user can be a medical staff such as a surgeon, a physician and/or a service technician.

The interface 105 can be a wireless interface 105 or a wired interface 105. In some embodiments, the interface 105 can be a Universal Serial Bus (USB) port, a serial port, a parallel port, or other data port capable of receiving the identification data.

The identification data is obtained from at least one of a portable component 110, a physical key, a biometric device and a user input.

The physical key comprises at least one of a physical signature, a magnetic signature and a digital signature. The biometric device comprises one of a fingerprint analyzer, a voiceprint analyzer, a retinal scanner, a brainwave scanner, a handwriting scanner, and a DNA sampler.

The portable component 110 may be one of an information tag operable to be attached to the user, a Universal serial bus (USB) storage device and a removable media configured for the purpose of transporting data from one medical device to another medical device.

The information tags are typically utilized for tagging and electronically identifying the user by reading the identification data stored in the information tag using contact-less radio-frequency (RF) transmissions. The information tag may be one of a radio frequency identifier (RFID), a barcode label and a magnetic stripe tag embedded in an adhesive tag that adheres to the user in a tamper resistant fashion.

In one embodiment, the use of the portable component 110 for procuring the identification data may be in conjunction with a user input. The user input can be a user login via an input device such as a keypad, a keyboard, a touch pad, a light pen, a laser pen and a microphone.

Further, each user login can correspond to a single user set. The identification data provided by the user login can be from one of the user belonging to the user set. The identification data of a particular user from the user set can be provided by the portable component 110.

In an alternate embodiment, the identification data from the portable component 110 can enable a user to gain direct access to the medical device 100, in a scenario where the user is unable to gain access to the medical device 100 through the user input.

In addition to storing the identification data, the portable component 110 can also be configured for storing the configuration data concerning the medical device 100. Further, the portable component 110 used for storing the identification data can be different from the portable component 110 employed for storing the configuration data. The portable component 110 is operable to wirelessly couple to the medical device 100 for transferring and receiving information to and from the medical device 100.

In one embodiment, the user specific configuration data can be manually recorded (e.g., on paper or a separate device) via the input device such as a wired or wireless keyboard, a touch-screen keyboard, or via a removable memory device. Subsequently the user specific configuration data can be transferred and/or programmed onto the portable component 110 via the interface 105. The portable component 110 can be associated with the user (e.g., patient, surgeon, or service technician) via, for example, a photograph, an identification number, or biometric data incorporated into the portable component 110. As an alternative, prior recorded configuration data can be electronically transferred to the portable component 110 in any manner known to those having skill in the art.

In one embodiment, the identification data can be obtained from the portable component 110 and a user specific configuration data can then be retrieved from one of a local area network or a PACS enabled network, such as a hospital network, based on the identification data.

The medical device 100 is communicatively coupled with the hospital network via a communication link. The communication link may be a wired or a wireless communication link or a combination thereof. The medical device 100 and the hospital network may communicate with each other using any suitable communication technology and/or protocol including, but not limited to, Ethernet, USB, TCP/IP, Bluetooth, ZigBee, Wi-Fi, Wireless USB, and the like. Additionally, the communication link may form a portion of a larger network including, for example, a publicly accessible global network such as the Internet.

In an exemplary embodiment, where only the identification data is provided, for example in a scenario where a biometric device is used for providing the identification data, with no configuration data, or partial configuration data, additional user-specific configuration data may be retrieved either from a local storage, portable component 110, or via a network connection, such as over the hospital network.

In one embodiment, the user specific configuration data may include a default setting of the medical device 100 or one of a number of standardized settings provided by the manufacturer of the medical device 100.

The controller 115 of the medical device 100 is configured for retrieving the configuration data from the portable component 110 based on the identification data provided by the user. The controller 115 is further operable to configure the medical device 100 based on the configuration data.

In an exemplary embodiment, the medical device 100 can be configured and/or data-populated by an information tag associated with a user. The information tag can comprise the desired configuration data of the user for a particular medical device 100 and/or a particular medical procedure and can also be preprogrammed via the input device and/or the interface 105. In addition, the information tag can store, for example, information desired by the user for a particular patient, medical device 100, date and time of the medical procedure or a default configuration for one or more medical devices.

Although the embodiment is described with reference to a single medical device 100, it is contemplated to be within the scope of the invention that a single portable component 110 can contain information for configuring and programming or data-populating multiple medical devices. For example, when a medical procedure requires more than one medical device, the portable component 110 can be configured to store the configuration data for, and can be used to configure and data-populate, more than one medical device.

Further, the portable component 110 can also be operable to receive a modified configuration data from the medical device 100 and store the modified configuration data, for example, in response to a user's saving the modified configuration data. Accordingly, the configuration data including the calibration and diagnostic data and software upgrades can be transferred between the medical device 100 and the portable component 110. The changes in the configuration data thus stored in the portable component 110 can be used in subsequent medical procedures performed on different medical devices.

The portable component 110 may further include an overwrite protection feature whereby the data stored therein may be protected from being overwritten or changed, thereby providing a measure of security.

Each writing of the data to the portable component 110 is replicated in the record stored in a relational database. Compiling records of the data written to the portable component 110 in the relational database is particularly advantageous in enabling the retrieval of the data when the portable component 110 is misplaced, lost or stolen, or if the data stored in the portable component 110 is changed or corrupted or lost for any reason.

Embodiments of this invention can be used, without limitation, for patient data such as patient identification data, user's data such as a user specific configuration data, device configuration and maintenance data such as medical device parameters associated with a desired medical procedure and/or a service technician's custom data such as device calibration data, maintenance data and upgrade data, etc.

Thus in one embodiment, the portable component 110 can include identification data and security data, calibration data to calibrate the medical device 100, and, in addition configuration data. The medical device 100 can automatically calibrate itself based on the received calibration data. Alternatively, the medical device 100 can be calibrated by the user using the received calibration data. Even further, the medical device 100 can be automatically configured (beyond calibration) based on the configuration data received from the portable component 110.

Figure 2:
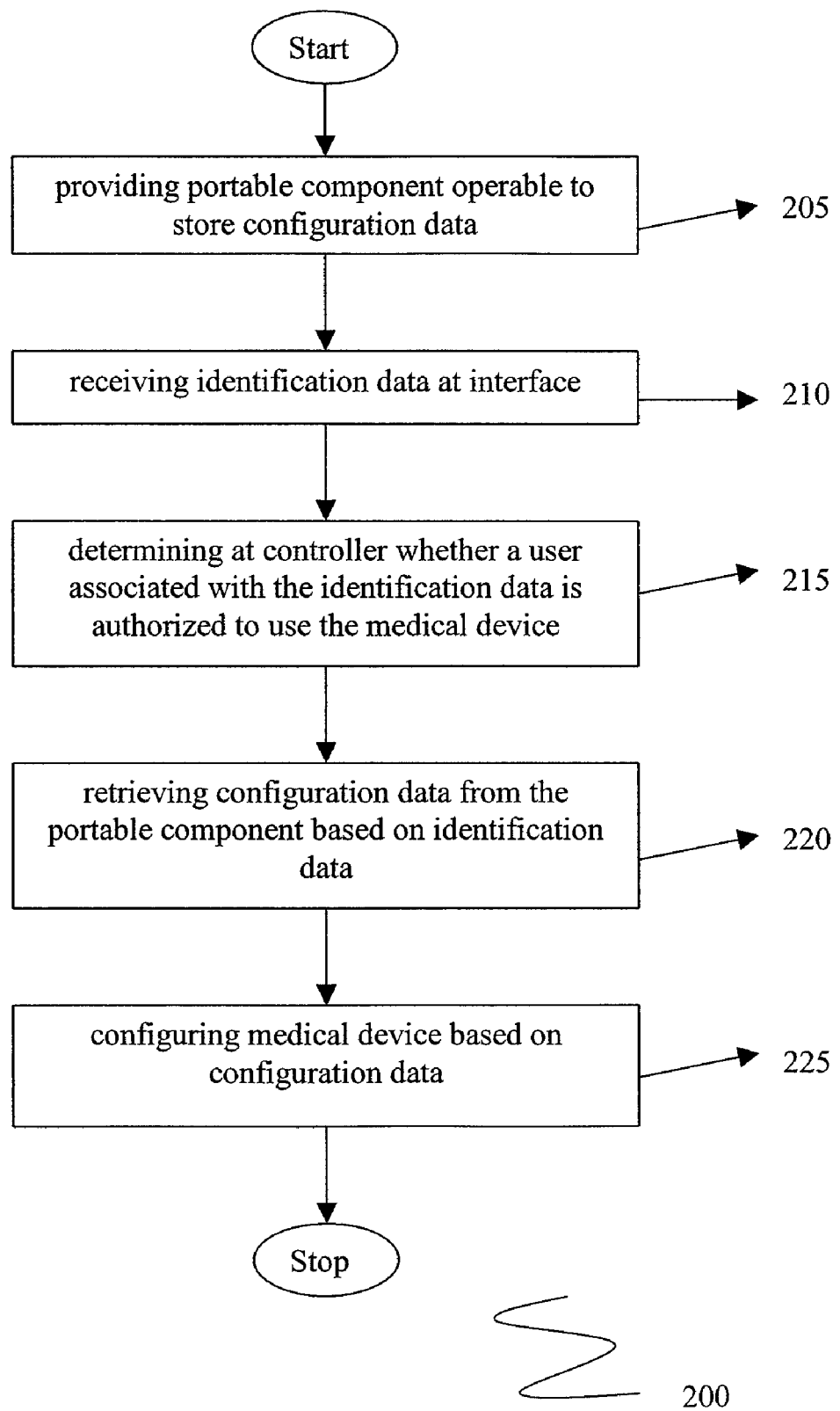
FIG. 2 shows a flow diagram of a method of configuring a medical device, in an embodiment.

In another embodiment, represented by FIG. 2, a method 200 for configuring the medical device 100 is provided. The method 200 comprises steps of providing the portable component 110 operable to store the configuration data step 205, receiving the identification data at the interface 105 operable to receive the identification data in the medical device 100 step 210, determining at the controller 115 in the medical device 100 whether a user associated with the identification data is authorized to use the medical device 100 based on the identification data received at the interface 105 step 215, retrieving the configuration data from the portable component 110 based on the identification data step 220 and configuring the medical device 100 based on the configuration data retrieved step 225.

Prior to the commence of a medical procedure, at the medical device 100, the configuration data stored in the portable component 110 can be transferred to the medical device 100, where it is operable to cause the medical device 100 to be preconfigured and data fields to be data-populated based on the configuration data stored in the portable component 110.

Further, the configuration data stored in the portable component 110 can be encrypted for providing a security function, such as determining whether the surgeon, medical staff or the technician is authorized to use the medical device 100. Accordingly the portable component 110 may include data for logging the user on to the medical device 100, transferring the custom machine settings of the user and configuring the medical device 100 in accordance with the custom machine settings.

Based on the identification data provided by the user, the controller 115 can determine whether the user is authorized to use the medical device 100. The medical device 100 can further include a memory unit for storing criteria, such as a corresponding set of authorized codes or data, an algorithm, formula or other predefined criteria (generally "algorithm").

The memory unit can be a memory element that is readily accessible or a memory element that is integrated within other components of the medical device 100, depending on security requirements.

The controller 115 is a processor or a microcontroller, programmed with software or hardware that processes the identification data received at the interface 105 and the criteria stored in memory unit to determine, for example whether the identification data received at the interface 105 is associated with an authorized user. The controller 115 is further configured to enable or disable the medical device 100 based on the match between the identification data and the criteria. The controller 115 can be configured to subsequently retrieve the configuration data, corresponding to the identification data, from the portable component 110, upon determining the authorized user. Further, the controller 115 can be operable to generate control signals to configure the medical device 100 and data-populate selected data fields in accordance with the configuration data.

In one embodiment, the user specific configuration data may include a workflow plan, for example, an ordered selection of instructional images that are displayed to the user via a display device such that the instructional images provide a "walk-through" of the medical procedure or a portion thereof. Alternatively, the workflow plan may include a number of surgical sub-step images, some of which may or may not be displayed to and performed by the surgeon based on selections chosen by the surgeon during the performance of a surgical procedure.

This embodiment, may be applied generally to areas of surgery where configuring and data-populating a surgical device prior to a surgical procedure may be desired. Nevertheless, embodiments of the invention can be used to configure a non-surgical equipment in an analogous manner.

Further, during the performance of the medical procedure, the controller 115 may be configured to determine deviations of the user from the determined workflow plan and record such deviations. Additionally, the controller 115 may be configured to record the selections made by the user and screenshots of the images displayed to the user during the performance of the medical procedure. Furthermore, the controller 115 may also record notes provided by user during the medical procedure. The user may provide verbal notes using a microphone and/or text notes via any other input device such as a wired or wireless keyboard, a touch-screen keyboard, or via a removable memory device. The controller 115 may record the notes by, for example, storing the text and/or voice communication data in the memory device and/or the portable component 110.

Upon completing the medical procedure, the controller 115 may be configured to store the configuration data on the hospital network (e.g., in a database) via the communication link. The configuration data may include, but is not limited to, the pre-operative data, the patient-related data, the procedure-specific data, deviation data indicative of the deviations of the user from the workflow plan, verbal or other notes, data indicative of selections made by the user during the medical procedure, and/or screenshots of images displayed to the user during the performance of the medical procedure.

Accordingly, it should be appreciated that the controller 115 is configured to determine a workflow plan for the chosen medical procedure based on decisions and/or selections of the user chosen prior to the performance of the medical procedure.

The controller 115 may be configured to automatically store the configuration data in the database upon completion of the medical procedure or the configuration data may be stored upon authorization by the user for later retrieval. In this way, the configuration data may be temporarily stored in the memory device of the medical device 100, the portable component 110, a hard drive, or other data storage device coupled with or included in the medical device 100 and subsequently uploaded to the hospital network for archival storage.

In some embodiments, the stored configuration data may be downloaded from the hospital network to a remote information management system via the communication link. For example, the user may download the configuration data to a remote computer located in the user's office. Additionally, the user may supplement the configuration data with additional notes, diagrams, or comments by uploading such data from the remote computer to the hospital network for storage in, for example, the database. The uploaded data may be stored in relation to the configuration data such that the uploaded data becomes a permanent or linked portion of the configuration data.

In yet another embodiment an algorithm to be executed by the medical device 100 for assisting a user in performing a medical procedure may be provided. The algorithm may be embodied as a software program stored in the memory device and executed by the controller 115 of the medical device 100.

The algorithm can be a computer program product stored in a computer readable media for providing a method 200 for configuring the medical device 100. The computer program product comprises a routine for receiving the configuration data from the portable component 110, a routine for receiving the identification data at the interface 105 operable to receive the identification data in the medical device 100, a routine for determining at the controller 115 in the medical device 100 whether the user associated with the identification data is authorized to use the medical device 100, based on the identification data received at the interface 105, a routine for retrieving the configuration data from the portable component 110 based on the identification data and a routine configuring the medical device 100 based on the configuration data retrieved.

The computer program product can be a tangible record in one or more of a printed document, a computer floppy disk, a computer CD-ROM disk, or any other desired medium. The computer program product can be stored in a computer readable medium, such as a floppy disk, a CD-ROM disk, a removable disk and other computer readable files.

It is to be understood that the embodiments described herein may be implemented in various forms of hardware, software, firmware, special purpose processors, or combinations thereof. In one exemplary embodiment, the method 200 described herein is implemented in software as application comprising program instructions that are tangibly embodied on one or more program storage devices (e.g., hard disk, magnetic floppy disk, RAM, CD ROM, DVD, ROM and flash memory), and executable by any device or machine comprising suitable architecture. It is to be further understood that, because the constituent method steps, depicted in the accompanying Figures, can be implemented in software, the actual flow of the process steps may differ depending upon the manner in which the application is programmed. Given the teachings herein, one of ordinary skill in the related art will be able to contemplate these and similar implementations or configurations of the invention.

Further, the method 200 may be readily implemented in the form of computer software instructions executed by a system in a medical facility. The system may be a computer, a medical workstation, an imaging modality such as an ultrasound system, a computed tomography system, a magnetic resonance imaging system and an X ray system, an imaging server unit, a picture archival and communication system (PACS) and a medical information system such as a hospital information system (HIS), a laboratory information system (LIS), a clinical information system (CIS), a radiology information system (RIS), and the like.

The above-description of the embodiments of the system 100, the method 200 and the computer readable storage medium have the technical effect of configuring a medical device 100, that reduces the need for user interaction with the medical device 100 thereby helping the user to carry out a medical procedure.

Embodiments of the invention provide increased reliability and functionality over the prior art, thus improving the effectiveness and safety of a medical procedure by helping to ensure that the user specific configuration data for a medical device and/or a medical procedure are accurately and efficiently entered into the medical device.

The method of configuring the medical device provides an improved understanding, relevancy, and/or visibility of a user selected informational subsets thereby reducing screen clutter and improving usage of screen real estate.

The method of configuring the medical device reduces the need for user interaction with the medical device, which is of particular value in the sterile and time-critical surgical setting. Further, the method of automatically configuring the medical device facilitates a general "ease-of-use product" perception.

In embodiments where the portable component provides a direct access to the medical device, the method eliminates the need to remember usernames and passwords, as is the case with login-based systems.

The portable components operable to carry the configuration data eliminate the need to store or transport configuration data on the local hospital network to maintain uniformity across different physical systems. This is advantageous when updates are made on a system that is not connected to the hospital network. This further eliminates the need to transfer the configuration data from one hospital network to another when a user practices with different systems at different sites.

In various embodiments, system and method for configuring a medical device are described. However, the embodiments are not limited and may be implemented in connection with different applications. The application of the invention can be extended to other areas, for example a workflow involving, sharing any type of protected or private information. The invention provides a broad concept of providing configuration data in a portable component for enabling configuration of a medical device, which can be adapted in a medical institution, such as a hospital, clinic, research facility, university, pharmaceutical company, governmental organization and the like. Accordingly, the invention is not limited to a hospital setting. The design can be carried further and implemented in various forms and specifications.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A medical device, comprising:
an interface configured to receive identification data for a user;

a portable component configured to store configuration data for the medical device and security data for the user; and a controller configured to determine whether a user associated with the identification data is authorized to use the medical device based on the identification and security data received at the interface, the controller further configured to retrieve the configuration data from the portable component based on the identification data and to configure the medical device based on the configuration data.

2. The medical device of claim 1, wherein the portable component is an RFID tag operable to be attached to a user.

3. The medical device of claim 1, wherein the portable component is one of a Universal Serial Bus (USB) storage device and a removable media.

4. The medical device of claim 1, wherein the identification data is obtained from at least one of the portable component, a physical key, a biometric device and a user input.

5. The medical device of claim 1, wherein the identification data is obtained from a physical key, and the physical key comprises one of a physical signature, a magnetic signature and a digital signature.

6. The medical device of claim 1, wherein the identification data is obtained from a biometric device, and the biometric device comprises one of a fingerprint analyzer, a voiceprint analyzer and a retinal scanner.

7. The medical device of claim 1, wherein the medical device is a surgical device.

8. The medical device of claim 1, wherein the interface is a transceiver operable to receive and transmit data.

9. The medical device of claim 8, wherein the interface is operable to program the portable component with a modified configuration data, and the portable component is operable to receive and store the modified configuration data.

10. The medical device of claim 1, wherein the portable component is also configured to store the identification data.

11. The medical device of claim 10, wherein the portable component is also configured to store calibration data for the medical device.

12. A method for configuring a medical device, the method comprising:

receiving identification data and security data at an interface operable to receive the identification data in the medical device;

determining at a controller in the medical device whether a user associated with the identification data is authorized to use the medical device based on the identification and security data received at the interface;

retrieving configuration data from a portable component based on the identification data; and configuring the medical device based on the configuration data retrieved.

13. The method of claim 12, wherein the portable component is an RFID tag operable to be attached to the user.

14. The method of claim 12, wherein the portable component is one of a USB storage device and a removable media.

15. The method of claim 12, wherein the identification data is obtained from at least one of the portable component, a physical key, a biometric device and a user input.

16. The method of claim 12, wherein the identification data is obtained from a physical key, and the physical key comprises one of a physical signature, a magnetic signature and a digital signature.

17. The method of claim 12, wherein the identification data is obtained from a biometric device, and the biometric device comprises one of a fingerprint analyzer, a voiceprint analyzer and a retinal scanner.

18. The method of claim 12, wherein the medical device is a surgical device.

19. A computer program product stored in a computer readable media for providing a method for configuring a medical device, the computer program product comprising:

a routine for receiving configuration data stored in a portable component;

a routine for receiving identification data and security data at an interface operable to receive the identification data in the medical device;

a routine for determining at a controller in the medical device whether a user associated with the identification data is authorized to use the medical device based on the identification data and security data received at the interface;

a routine for retrieving the configuration data from the portable component based on the identification data; and a routine for configuring the medical device based on the configuration data retrieved.

20. The computer program product of claim 19, wherein the portable component is an RFID tag operable to be attached to the user.

21. The computer program product of claim 19, wherein the portable component is one of a Universal serial bus (USB) storage device and a removable media.

22. The computer program product of claim 19, wherein the identification data is obtained from at least one of the portable component, a physical key, a biometric device and a user input.

23. The computer program product of claim 19, wherein the identification data is obtained from a physical key, and the physical key comprises one of a physical signature, a magnetic signature and a digital signature.

24. The computer program product of claim 19, wherein the identification data is obtained from a biometric device, and the biometric device comprises one of a fingerprint analyzer, a voiceprint analyzer and a retinal scanner.

25. The computer program product of claim 19, wherein the medical device is a surgical device.

* * * * *